(12) United States Patent
Amir et al.

(10) Patent No.: US 9,965,657 B1
(45) Date of Patent: May 8, 2018

(54) DISPOSABLE PATIENT TAG

(71) Applicant: CenTrak Inc., Newtown, PA (US)

(72) Inventors: Israel Amir, Newtown, PA (US); Ari Naim, Tenafly, NJ (US)

(73) Assignee: CENTRAK, INC., Newton, PA (US)

( * ) Notice: Subject to any disclaimer, the term of this patent is extended or adjusted under 35 U.S.C. 154(b) by 235 days.

(21) Appl. No.: 14/594,248

(22) Filed: Jan. 12, 2015

Related U.S. Application Data

(60) Provisional application No. 61/964,651, filed on Jan. 10, 2014.

(51) Int. Cl.
  G08B 23/00 (2006.01)
  G06K 7/10 (2006.01)

(52) U.S. Cl.
  CPC ................... G06K 7/10009 (2013.01)

(58) Field of Classification Search
  None
  See application file for complete search history.

(56) References Cited

U.S. PATENT DOCUMENTS

| | | | | |
|---|---|---|---|---|
| 4,579,216 A * | 4/1986 | DeWoolfson | ......... | G07F 7/0609 100/902 |
| 6,169,483 B1 * | 1/2001 | Ghaffari | ............... | G06Q 10/087 340/568.1 |
| 8,387,771 B2 * | 3/2013 | Boydston | .............. | G07F 7/0609 194/205 |
| 9,245,404 B1 * | 1/2016 | Martuch | ................. | G07F 7/005 |
| 9,454,869 B1 * | 9/2016 | Martuch | ................. | G07F 7/005 |
| 2011/0089230 A1 * | 4/2011 | Artino | ................ | G06Q 20/1085 235/379 |
| 2011/0266341 A1 * | 11/2011 | Artino | ................ | G06Q 20/1085 235/379 |
| 2013/0146657 A1 * | 6/2013 | Graef | .................... | G07F 19/203 235/379 |
| 2013/0339221 A1 * | 12/2013 | Gentelet | .............. | G06K 7/0008 705/39 |
| 2014/0131439 A1 * | 5/2014 | Graef | .................... | G06Q 40/02 235/379 |
| 2014/0166745 A1 * | 6/2014 | Graef | .................... | G07F 19/202 235/379 |
| 2014/0214697 A1 * | 7/2014 | McSweeney | ........... | B65F 1/004 705/308 |
| 2014/0368318 A1 * | 12/2014 | Paris, Jr. | ............ | G06K 7/10009 340/10.1 |

* cited by examiner

Primary Examiner — Julie Lieu

(74) Attorney, Agent, or Firm — Maldjian Law Group LLC

(57) ABSTRACT

An apparatus, system and method to track location, the apparatus including: a substantially planar disposable housing comprising an electronics compartment; a secondary technology sensor disposed along a periphery of the disposable housing; an electronics module disposed within the electronics compartment, the electronics module comprising: a processor coupled to a memory; an RF transceiver coupled to an RF antenna and to the processor; a secondary technology transceiver coupled to the processor; and a battery coupled to the apparatus, wherein the battery is not field-replaceable. The apparatus may further include a marking to indicate a predetermined period of time that the apparatus is operable. Embodiments further include an unattended smart container to autonomously collect a plurality of the apparatus and to report status to a central monitor system.

40 Claims, 6 Drawing Sheets

200

400

500

800

DISPOSABLE PATIENT TAG

CROSS-REFERENCE TO RELATED APPLICATIONS

This application claims the benefit of U.S. Provisional Patent Application Ser. No. 61/964,651, filed on Jan. 10, 2014, the entire content of which is hereby incorporated by reference in its entirety.

BACKGROUND

Field of the Invention

Embodiments in accordance with the present invention relate to a disposable apparatus to track a position, and in particular to track a position of a patient in a hospital.

Description of Related Art

Indoor Real-Time Location (RTL) Systems (RTLS) are popular in the healthcare industry for a variety of applications ranging from asset tracking through patient and staff tracking, environmental or patient sensing (e.g., temperature), hygiene compliance, elopement (i.e., a patient leaving a facility without authorization), theft prevention, and so forth. A need for efficient and affordable patient tracking is important to more efficient and better healthcare.

RTLS systems of the known art rely primarily upon RF transmissions to determine location. The known RTLS may further utilize a secondary technology such as infrared (IR) and/or ultrasound (US) in order to improve spatial resolution relative to RF triangulation based methods. Methods for using secondary technologies are described in numerous places, for example, in the following issued patents: U.S. Pat. Nos. 8,604,909, 8,046,486, and 5,917,425, all of which are incorporated by reference in their entireties. These patents describe RTLS methods that use IR and US as a secondary technology to improve location accuracy.

Technologies of the known art suffer drawbacks when used to try to implement patient tracking. For example, passive RFID tracking is typically limited to either crossing detection (e.g., using an RFID reader surrounding a door to detect when an RFID tag passes through the door), or manual scanning that is typically performed after the patient location is already known. Having additional RFID readers spread around the hospital and not just at doors increases the cost and may expose patients and equipment to relatively high doses of low frequency (LF), electromagnetic radio frequency (RF) fields.

Active RFID tags also are not a desirable solution. Active RFID tags are more expensive than passive RFID tags, which leads to problems in a hospital environment. First, patient tag loss (i.e., attrition) is estimated to be at least 10% a month. This results in turnover of substantially the entire inventory of active RFID patient tags every ten months. Second, conventional active RFID tags are often reused for another patient when the first patient no longer needs the tag. This reuse necessitates an anti-infection regiment that is both costly and must be as close to 100% reliable as possible.

Furthermore, patients typically already wear an identification band, bracelet or the like, which may include an additional barcode that is different than the ID coded into the active RFID tag. The two IDs may not always be assigned to the same patient, e.g., if the active RFID tag is reassigned to a later patient. It is advantageous at least for the sake of patient comfort that an apparatus to implement efficient and affordable patient tracking be able to be incorporated with the identification band, bracelet or the like that the patient may already be wearing.

Therefore, it would be desirable to have a simple and unified apparatus and method in order to continuously track patients in hospitals, such that the shortcomings of the current methods as identified above are overcome.

SUMMARY

An apparatus, system and method to track location, the apparatus including: a substantially planar disposable housing comprising an electronics compartment; a secondary technology sensor disposed along a periphery of the disposable housing; an electronics module disposed within the electronics compartment, the electronics module comprising: a processor coupled to a memory; an RF transceiver coupled to an RF antenna and to the processor; a secondary technology transceiver coupled to the processor; and a battery coupled to the apparatus, wherein the battery is not field-replaceable.

The preceding is a simplified summary of embodiments of the disclosure to provide an understanding of some aspects of the disclosure. This summary is neither an extensive nor exhaustive overview of the disclosure and its various embodiments. It is intended neither to identify key or critical elements of the disclosure nor to delineate the scope of the disclosure but to present selected concepts of the disclosure in a simplified form as an introduction to the more detailed description presented below. As will be appreciated, other embodiments of the disclosure are possible utilizing, alone or in combination, one or more of the features set forth above or described in detail below.

BRIEF DESCRIPTION OF THE DRAWINGS

The above and still further features and advantages of the present invention will become apparent upon consideration of the following detailed description of embodiments thereof, especially when taken in conjunction with the accompanying drawings wherein like reference numerals in the various figures are utilized to designate like components, and wherein.

Figure 1:
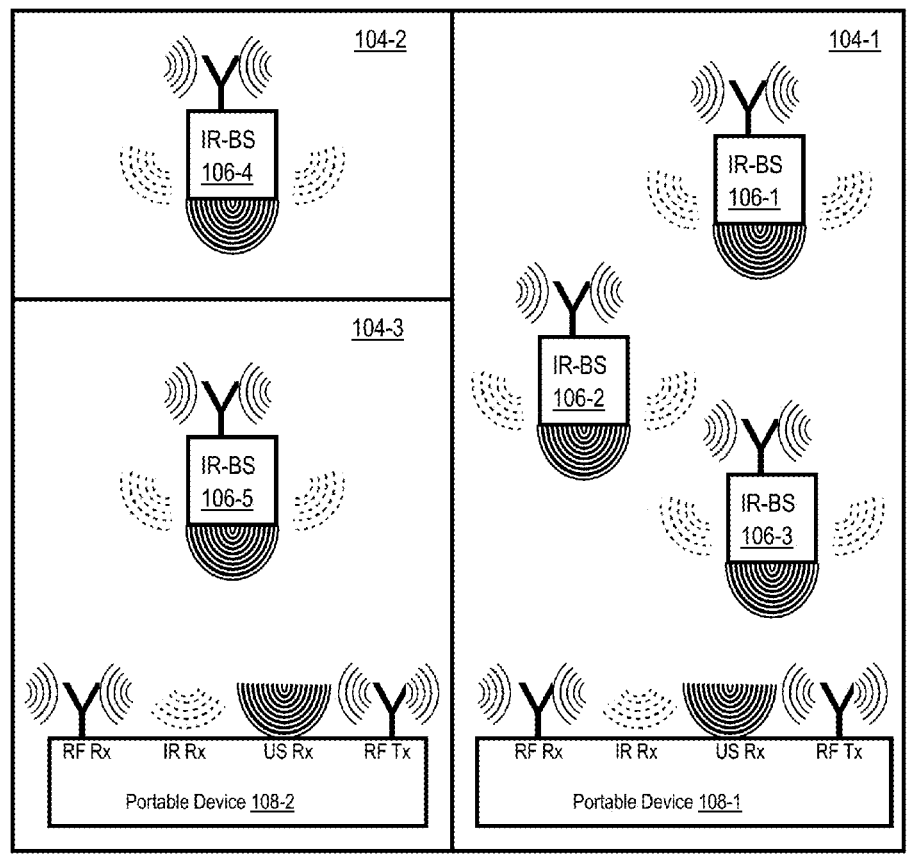
FIG. 1 is a block diagram of a system for locating and identifying portable devices in an enclosure, according to an embodiment of the present disclosure.
Figure 1:
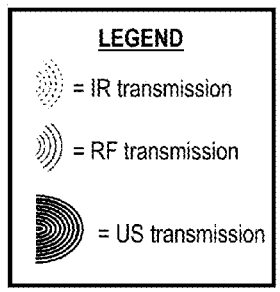
Figure 1:
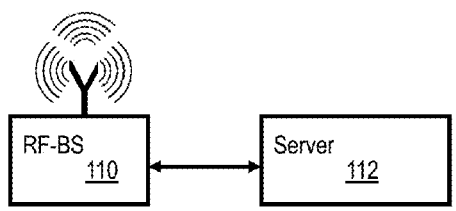

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures. Optional portions of the figures may be illustrated using dashed or dotted lines, unless the context of usage indicates otherwise.

DETAILED DESCRIPTION

The disclosure will be illustrated below in conjunction with an exemplary communication system. Although well suited for use with, e.g., a system using a server(s) and/or database(s), the disclosure is not limited to use with any particular type of communication system or configuration of system elements. Those skilled in the art will recognize that the disclosed techniques may be used in any communication application in which it is desirable to utilize location sensors that communicate with a central monitor.

The exemplary systems and methods of this disclosure may also be described in relation to software, modules, and associated hardware. However, to avoid unnecessarily obscuring the present disclosure, the following description omits well-known structures, components and devices that may be shown in block diagram form, are well known, or are otherwise summarized.

In the following detailed description, numerous specific details are set forth in order to provide a thorough understanding of embodiments or other examples described herein. In some instances, well-known methods, procedures, components and circuits have not been described in detail, so as to not obscure the following description. Further, the examples disclosed are for exemplary purposes only and other examples may be employed in lieu of, or in combination with, the examples disclosed. It should also be noted the examples presented herein should not be construed as limiting of the scope of embodiments of the present invention, as other equally effective examples are possible and likely.

As used herein, the term "Wi-Fi" or "conventional Wi-Fi" refers generally to a bi-directional radio communication technology that operates based on one or more of the Institute of Electrical and Electronics Engineers (IEEE) 802.11 family of standards, which are incorporated herein by reference. The IEEE 802.11 standards specify the RF and protocol characteristics of a bi-directional radio communication system.

As used herein, the term "module" refers generally to a logical sequence or association of steps, processes or components. For example, a software module may comprise a set of associated routines or subroutines within a computer program. Alternatively, a module may comprise a substantially self-contained hardware device or circuit device. A module may also comprise a logical set of processes irrespective of any software or hardware implementation.

As used herein, the term "transmitter" may generally comprise any device, circuit, or apparatus capable of transmitting an electrical, electromagnetic, infrared, ultrasonic, or optical signal. As used herein, the term "receiver" may generally comprise any device, circuit, or apparatus capable of receiving an electrical, electromagnetic, infrared, ultrasonic, or optical signal. As used herein, the term "transceiver" may generally comprise any device, circuit, or apparatus capable of transmitting and receiving an electrical, electromagnetic, infrared, ultrasonic, or optical signal.

The term "computer-readable medium" as used herein refers to any tangible storage and/or transmission medium that participates in storing and/or providing instructions to a processor for execution. Such a medium may take many forms, including but not limited to, non-volatile media and volatile media. Non-volatile media includes, for example, NVRAM, flash media, or magnetic or optical disks. Volatile media includes dynamic memory, such as main memory. When the computer-readable media is configured as a database, it is to be understood that the database may be any type of database, such as relational, hierarchical, object-oriented, and/or the like.

RTL systems are known that include base stations that transmit IR signals (i.e., IR base stations) with their respective base station ID (BS-ID) to portable devices that are equipped with IR receivers. Upon reception of a BS-ID, the portable device transmits both the device ID and the received BS-ID to a reception device, for example, by radio frequency (RF) or IR transmission. The RTL system may include a server that associates the BS-ID with the device ID (received from the portable device by the reception device). In this manner, the position of the portable device may be displayed as the position of the IR base station. In exemplary implementations, both base stations and tags are battery operated.

Embodiments in accordance with the present disclosure relate to apparatus, system, and methods for tracking in general, and in particular to tracking of patients or other people in a hospital environment. Embodiments are also useful for tracking physical assets such as medical equipment. Embodiments include several features, which may be used individually or in combination:

(a). Embodiments use innovative, low-cost, disposable packaging that is suitable for a single use or a small number of uses;

(b). Embodiments are designed using low-cost electronics, suitable for a disposable design;

(c). Embodiments may be provided as an ID bracelet that may be integrated with a traditional barcode based bracelet by use of innovative integration features;

(d). Embodiments may provide an integrated timer in order to help reduce reuse or excessive use of the embodiment, and thus reducing a risk of infection. In some embodiments, the timer is designed to last for approximately 30 days before the disposable tag has to be either refurbished or discarded;

(e). Integrated timer to monitor on the shelf battery status.

(f). Embodiments provide a design that allows for low cost refurbishing of the tag;

(g). Embodiments help enable a business model that minimizes the overall cost of ownership, and is facilitated by the combination of a low cost design and lower cost of refurbishing a tag;

(h). Embodiments are able to integrate the disposable patient tag with an existing patient ID bracelet; and (i). Embodiments provide a design that allows for the use of substantially any commercial bracelet with the tag.

Although one embodiment of the invention is the disposable tag itself, embodiments also include a system that supports disposable, single-use or limited-use tags. Embodiments also include methods for system operation to use disposable, single-use or limited-use tags.

Referring now to FIG. 1, a block diagram is shown of a system 100 for determining a location and an identity of portable devices 108 in an enclosure 102. System 100 may include a plurality of IR and/or US emitters 106-1 ... 106-N ("emitter"), one or more portable devices 108 and at least one RF base station (RF-BS) 110. In some embodiments, RF base station 110 may be a Wi-Fi access point (i.e., an RF access point). An individual but unspecified emitter may be referred to as emitter 106 or emitter 106-n. The emitters may be referred to collectively as emitters 106. An individual but unspecified portable device may be referred to as portable device 106 or portable device 106-n. The portable devices may be referred to collectively as portable devices 106.

RF base station 110 may transmit timing synchronization information (TSI) signal, for example, in a beacon, to emitters 106 and portable devices 108 that are each equipped with RF transceivers, by RF transmission. The TSI may be used by emitters 106 to transmit a corresponding BS-ID, e.g., an IR location code, in a period of time after receiving the TSI. The period of time for emitters 106 to transmit the respective BS-ID signals may be fixed or transmitted as a part of the information carried by the beacon.

Enclosure 102 may include a plurality of separate zones 104, which typically coincide with individual rooms or zones within enclosure 102. For example, zone 104-1 represents a corridor. Each room or zone may be provided with at least one emitter 106. For example, corridor 104-1 includes emitters 106-1, 106-2, 106-3.

Portable devices 108 may be provided for persons or apparatuses. The portable devices 108 may include an IR receiver and an RF transmitter or transceiver which are coupled to each other. In this manner, the RF transceiver may receive the TSI and if so desired may transmit received BS-ID and its device ID at an RF carrier frequency to RF base station 110. Portable devices 108 further include an ultrasonic receiver.

The modulated carrier signal received by RF base station 110 may be decoded to reproduce the BS-ID and the device ID.

Figure 2:
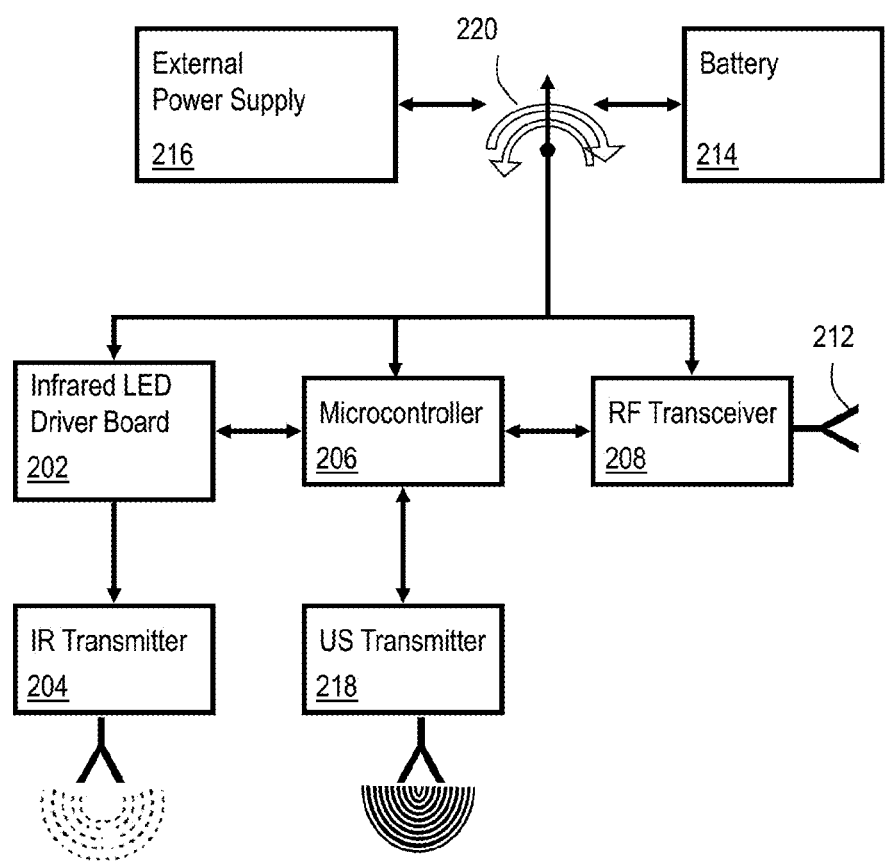
FIG. 2 is a functional block diagram of an infrared (IR) and ultrasound (US) emitter, according to an embodiment of the present disclosure.

FIG. 2 illustrates a block diagram of an embodiment 200 of emitter 106. Embodiment 200 includes a microcontroller 206 coupled to an IR driver board 202, which in turn is coupled to IR transmitter 204. Microcontroller 206 is further coupled to US transmitter 218 and may further be coupled to an RF transceiver 208, which in turn is coupled to an RF antenna 212. Active components are coupled to a power source such as battery 214 or external power supply 216 (e.g., conventional AC power). The power source optionally may be selected by switch 220.

Although not shown in FIG. 2, a base-station ID (BS-ID) associated with emitter 106 and/or its installed location may be stored by embodiment 200, for example, in a memory of microcontroller 206. Driver board 202 may be configured to transmit the associated BS-ID through IR transmitter 204. It is understood that IR transmitter 204 may include any device suitable for transmitting an IR burst that includes the associated ID.

Figure 3:
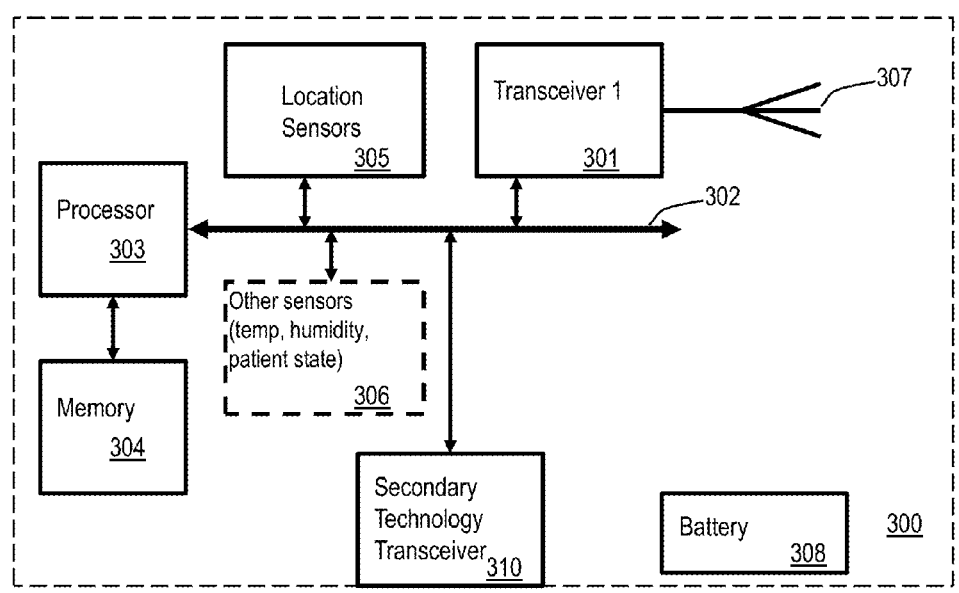
FIG. 3 is a functional block diagram depicting at a high level of abstraction a disposable tag in accordance with an embodiment of the present disclosure.

FIG. 3 illustrates at a high level of abstraction a block diagram of a tag 300 in accordance with an embodiment of the present invention. Tag 300 includes a transceiver 301, which may function as, e.g., a Wi-Fi communication interface. Transceiver 301 may be communicatively coupled via data bus 302 with processor 303. Processor 303 is communicatively coupled with memory 304. Memory 304 may be configured to store data, configuration settings, and the like, and to store instructions that, when performed by processor 303, cause tag 300 to perform functions described herein. Tag 300 may further include one or more of location sensors 305 and/or optional environmental sensors 306. Location sensors 305 may utilize secondary technology and associated secondary technology transceiver 310 as described herein, for the purpose of position determination. Secondary technology transceiver 310, when used as a receiver, may include a sensor (e.g., IR photodiode, US transducer, etc.), coupled to circuitry to process raw signals from the sensor. Secondary technology transceiver 310, when used as a transmitter, may include an emitter (e.g., IR LED, piezoelectric material, etc.), coupled to circuitry to provide driving signals to the emitter. Optional environmental sensors 306 may include sensors related to patient vital signs, patient state, the environment in the vicinity of the patient, and so forth. Sensors 305, 306 may be communicatively coupled via data bus 302 with processor 303. Transceiver 301 is coupled to antenna 307 for transmission and/or reception of RF signals. A battery 308 is used to provide electrical power to components of tag 300. Persons of skill in the art will realize that the high-level depiction of FIG. 3 omits certain known features such as internal circuitry, and so forth.

Electronic Hardware Design

Embodiments in accordance with the present disclosure simplify the electronic design by eliminating a motion sensor that typically would be used to increase battery life. Although this shortens battery life of the disposable tag, compared to usage of the same or similar battery with a tag that includes a motion sensor, the shortened battery life and limited-time operation is still sufficient to encompass the amount of time that the disposable tag is expected to be used by a single patient.

In some embodiments, the tag battery is not field-replaceable. Such tags would have to be either discarded or refurbished at a service center when the battery depletes. If the battery is replaced at a service center, refurbishment may include disinfection of the tag so that the tag can be safely reused. Preventing field replacement reduces the risk of improper reuse for another patient without sufficient infection control. Preventing field replacement may be accomplished, for example, by soldering the battery directly to the tag or its circuitry. Preventing field replacement also may be accomplished by designing the circuitry to cease operation if the battery is removed, such that even after a new battery is installed, the circuitry has to be reset at a service center.

In order to make effective use of limited-time operation, improved methods to initiate operation of the disposable tag should be used. In one embodiment of the current invention, a control (e.g., a button press on the tag) may be used to wake the tag from a sleep state and start an active state. The control may be activated by, e.g., an attendant when the attendant places the disposable tag on the patient. In order to reduce the likelihood of erroneous or accidental tag wakeup, an aspect of time may be required with the control for successful activation. For example, the disposable tag may require multiple consecutive button presses within a limited period of time, e.g., two button presses with a minimum spacing of one second and maximum of three seconds. In another example, a long button press, say greater than three seconds is required to wake up the tag. In another example, a predetermined pattern of longer button presses and shorter button presses may be required, e.g., a long press followed within a predetermined time period by a relatively shorter button press.

In addition to using RF as a primary wireless communication technology, embodiments of the disposable tag may also include a secondary communication capability to support RTLS operation. For example, the secondary communication capability of the disposable tag may include one or more of the following:

(a). Infrared Receiver (IR) - a disposable tag using IR as a secondary receive technology will be compatible with base-stations that transmit IR signals as a secondary technology;

(b). Infrared Transmitter - a disposable tag using IR as a secondary transmit technology will be compatible with base-stations that receive IR signals as a secondary technology;

(c). Ultrasound Receiver (US) - a disposable tag using US as a secondary receive technology will be compatible with base-stations that transmit US signals as a secondary technology; and (d). Ultrasound Transmitter - a disposable tag using US as a secondary transmit technology will be compatible with base-stations that receive US signals as a secondary technology.

Operational Design

RTLS systems often are synchronized systems. In such systems, a secondary technology emitter such as a base station transmits its signals in predefined time slots. Tags can be synchronized in such systems by receiving synchronization signals using their separate RF receivers.

However, in order to reduce tag costs, it is desirable to utilize a simple uni-directional RF transmitter on the disposable tag. But a uni-directional synchronized system that utilizes only RF transmitters on the disposable tag is generally not feasible without more. For example, the disposable tag must search periodically for IR/US signals, and this can quickly deplete the tag battery if the disposable tag is not synchronized. To avoid excessive battery depletion, once the disposable tag finds the IR signal, the disposable tag can predict the next time that it has to energize its receiver in order to detect the IR/US signals. However, if the disposable tag stops receiving the IR/US signal after a predefined time, then the disposable tag will immediately start searching again for the IR/US signal. The search of IR/US may be designed to be periodic, for example, searching for three seconds in a 30-second period. Searching involves activating receiver circuitry in the disposable tag, therefore without such energy-saving provision the tag battery may be depleted before its expected life time.

In one embodiment of the current invention, in order to alert users to an impending end-of-life condition of the tag, the disposable tag may include a timer that counts down a predetermined operating period of time (e.g., ten days). The disposable tag may transmit a warning message toward the end of the predetermined operating period of time (e.g., on the last day). The warning message may include a message that the disposable tag will run out of power soon, and may report an exact time at which the disposable tag will cease operating. The timer may be used by the disposable tag to enforce the shutdown at the indicated time. The end-of-life alert may be provided on the tag (e.g., by use of an LED) or through a monitoring system external to the disposable tag. The monitoring system may be implemented by server 112.

To facilitate very low cost of tag ownership, tag replacement may operate as follows. First, a user obtains a disposable tag (e.g., by purchase, or by being issued one at a hospital, etc.). Second, once the tag reaches its end-of-life, the user relinquishes the disposable tag. For example, the disposable tag may be shipped back to the vendor, service center, or the like for refurbishment. Third, a new or refurbished disposable tag is sent back to the user. A refurbished disposable tag will be sterilized, cleaned, battery replaced, and an operational timer may be reset.

In one embodiment in accordance with an embodiment of the present disclosure, the disposable tag may be sent to a user without a band used to couple the disposable tag to the user. Coupling may be by way of a wristband, lanyard or the like, coupled to the user. Coupling may also be to another object affixed to the patient, such as a cast, a brace, and so forth. The band may be added at the hospital by the user or an attendant of the user. In another embodiment of the current invention, the disposable tag may be delivered to a user already equipped with a band or other apparatus to coupled the disposable tag to the user.

A band that is usable with the disposable tag is ordinarily marked or coded with information about the patient. For example, the band may include barcode, QR code, or the like that identifies the patient and may be linked to other information about the patient such as a medical record. When the band is dispensed to a patient, there is a need to associate the band barcode (which is typically is associated with the patient) with an RTLS ID number of the disposable tag, which also may be in the form of a barcode.

In one embodiment of the current invention, a barcode scanner may scan both the band barcode and the RTLS barcode, and the system associates the two barcodes. Thereafter, when the system receives the disposable tag ID, the system associates the disposable tag ID with the band ID and the patient. This type of association is needed when the band source is different than the disposable tag source. At least some of these system functions may be implemented by server 112.

In some cases, the band ID may be printed at a hospital. In this case, the disposable tag ID may be scanned first, and the disposable tag ID may be used initially as the band/patient ID.

In yet another embodiment of the invention, the disposable tag does not display a visible label in order to save cost. The disposable tag ID may be read by the system prior to printing the band ID, and is then the disposable tag ID read by the system would be printed on the patient band along with other information on the patient band. At least some of these system functions may be implemented by server 112.

For embodiments in which the manufacturer of the disposable tag also supplies the band, the band ordinarily will include the disposable tag ID, either as a separate item of data or by way of assigning the band ID to be the same as the disposable tag ID.

Physical/Industrial Design

Figure 4:
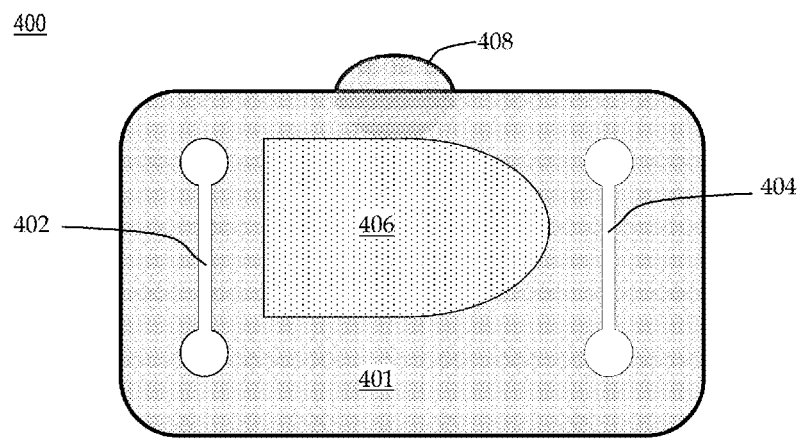
FIG. 4 illustrates physical aspects of a disposable tag in accordance with an embodiment of the present disclosure.

FIG. 4 illustrates physical aspects of embodiments in accordance with the present disclosure. FIG. 4 is not drawn to scale. Tag 400, illustrated in FIG. 4, is intended to be compatible with all known existing bracelets used in hospitals. Tag 400 includes a substantially planar body 401 that includes two slits 402, 404, which allow for simple and quick insertion of existing patient bands into and through tag 400. Slits 402, 404 may be arranged such that they are located near opposite lateral edges of body 401, and may extend along a substantial portion of the height of body 401, without significantly weakening the physical integrity of body 401. Slits 402, 404 may be arranged substantially parallel to each other. For example, a patient band may be inserted such that the patient band substantially covers tag 400 itself. Tag 400 further includes an electronics enclosure 406 which seals and protects the circuitry of tag 400 such as the circuitry illustrated in FIG. 3. Slits 402, 404 are of sufficient width and height to allow a patient band to pass through.

Tag 400 further includes a secondary technology sensor 408 (e.g., an IR sensor or a US sensor) that may protrude from the rest of body 401. Secondary technology sensor 408 is designed to protrude away from body 401 in order to avoid blockage of secondary technology sensor 408 by the patient band.

Physical dimensions of tag 400 should be large enough to provide acceptable communication link performance in view of antenna dimensions and the size of secondary technology sensors, and be easily locatable by an attendant, and be physically robust (e.g., thick enough to avoid being easily torn, punctured, etc.). However, tag 400 should be small enough to be unobtrusive to the patient. Tag 400 should be greater in height than the height of a patient band, with height being measured in a direction perpendicular to the direction that the patient band may be wrapped around a patient's limb. In some embodiments, tag 400 may be approximately one inch in height and two inches in length.

Figure 5:
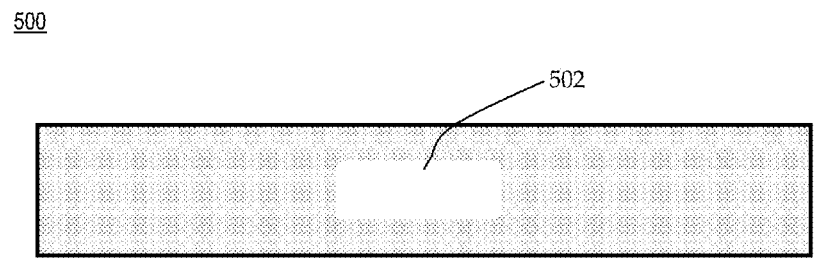
FIG. 5 illustrates a patient band capable of being coupled to a disposable tag, in accordance with an embodiment of the present disclosure.

Other embodiments of a disposable tag may attempt to reduce blockage of secondary technology by coupling it to a specially-configured patient band, and in particular to a patient band that incorporates an opening, aperture, or the like. FIG. 5 illustrates an embodiment of such a patient band 500, incorporating aperture 502. The opening or aperture 502 may conform to the size of a secondary technology sensor. Other shapes than that depicted in FIG. 5 may be used for aperture 502 for reasons of manufacturability or aesthetics, so long as the secondary technology sensor is not substantially blocked. In some embodiments, aperture 502 represents an empty space opening in patient band 500, such that there is no material within or covering aperture 502. In other embodiments, aperture 502 may represent a different material that is substantially transparent to secondary technology signals. The opening or aperture may be incorporated into the patient band during manufacture, or may be cut from the patient band at the time (or afterward) that the patient band is coupled to the disposable tag.

Figure 6:
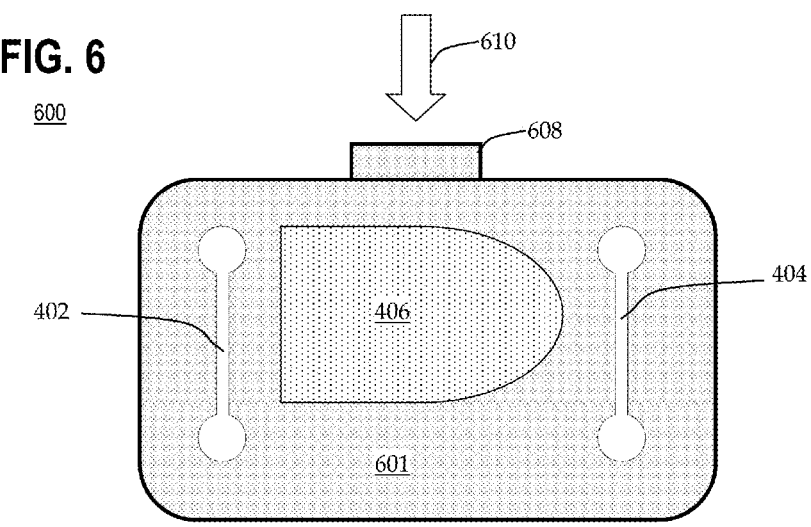
FIG. 6 illustrates physical aspects of a disposable tag in accordance with another embodiment of the present disclosure.

FIG. 6 illustrates tag 600 in accordance with an embodiment of the present disclosure. FIG. 6 is not drawn to scale. Tag 600 is similar to tag 400, but with the secondary technology receiver 608 configured to preferentially receive secondary technology signals 610 from a direction in the plane of substantially planar body 601.

Figure 7:
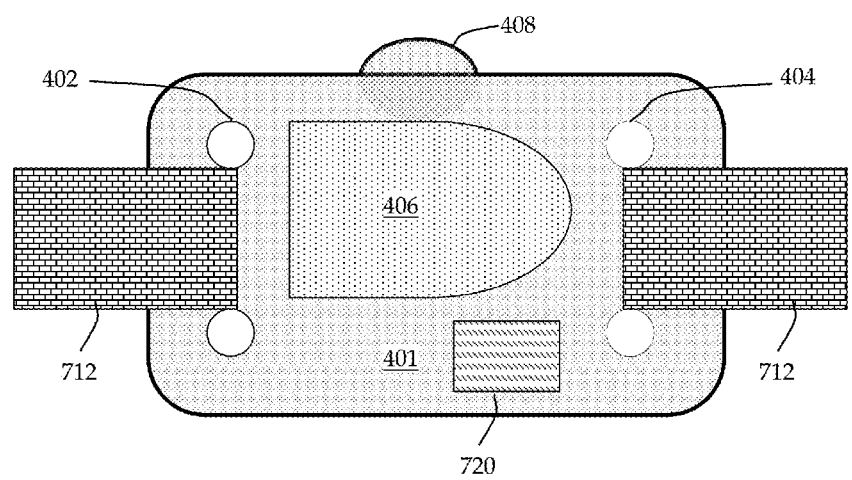
FIG. 7 illustrates a patient band coupled to a disposable tag, in accordance with an embodiment of the present disclosure.

FIG. 7 illustrates tag 400 coupled to patient band 712, in accordance with an embodiment of the present disclosure. FIG. 7 is not drawn to scale. FIG. 7 illustrates patient band 712 passing through slits 402, 402 and passing underneath body 401, i.e., between body 401 and the patient's body. Such a coupling of patient band 712 to tag 400 allows for reception of secondary technology signals by secondary technology sensor 408 with less likelihood of the secondary technology signals being blocked by patient band 712.

Embodiments in accordance with the present disclosure may utilize low-cost packaging in order to provide low cost of ownership. Extremely low-cost packaging is used because the relatively short battery life of the disposable tag leads to a short useful lifetime of the device and a high rate of disposal when the battery life has expired. In one embodiment of the invention, soft flexible vinyl such as that used for packaging consumer devices may be used. Such soft vinyl is ordinarily comfortable for patients to wear, even a sick patient, and is extremely low cost and lends itself well to quick refurbishment. Furthermore, soft vinyl may be well-sealed by using RF or US welding. During manufacture, slits 402, 404 may easily be cut, and no screws are needed.

Embodiments in accordance with the present disclosure include a business model that minimizes the overall cost of ownership, by facilitating refurbishment through a combination of a low-cost design with a lower cost of refurbishing a disposable tag. Cost of refurbishment includes costs to collect used disposable tags, repair and/or replace components as necessary (e.g., a battery), sterilization, repackaging, and inventory management to account for a refurbished disposable tag. Embodiments include disposable tag design features, and methods of accepting and recognizing a disposable tag designated for refurbishment.

Figure 8:
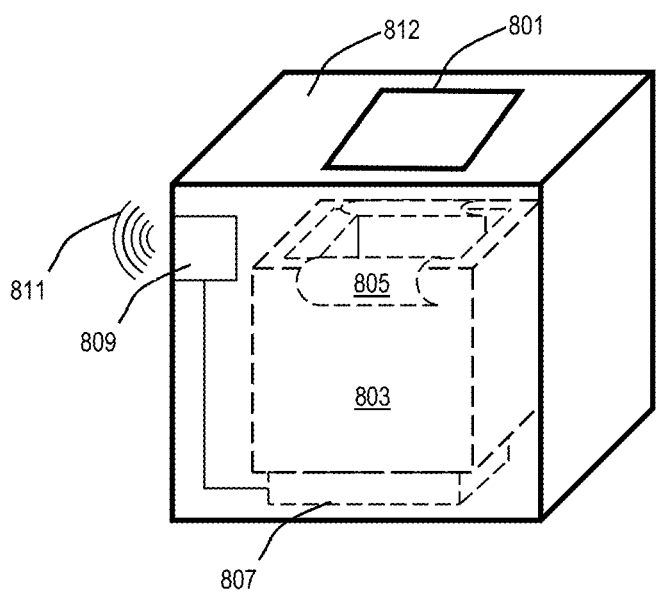
FIG. 8 illustrates a perspective view of a dropbox in accordance with an embodiment of the present disclosure.

For example, a method to facilitate refurbishment of a disposable tag may include providing drop boxes for depositing disposable tags destined for refurbishment. FIG. 8 illustrates an embodiment of a drop box 800 in accordance with an embodiment of the present disclosure. A wall 812 of drop box 800 includes a closeable opening 801 (e.g., a door, a slit cover opening, or the like) through which disposable tags destined for refurbishment may be deposited into drop box 800. Wall 812 may be considered to be any surface of drop box 800, including a side surface or a top surface. FIG. 8 illustrates wall 812 as a top surface of drop box 800.

Drop box 800 may include features that improve efficiency in scheduling collections from drop box 800. For example, drop box 800 may include a detection apparatus 807 that indicates a status of drop box 800, such as how many disposable tags are presently in drop box 800 and how long since drop box 800 was emptied or reset. The number of disposable tags in drop box 800 may be determined by detection apparatus 807 by, e.g., actual count when disposable tags are deposited, or estimated by weight from a scale, or estimated by volume (e.g., percentage filled). Detection apparatus 807 may include one or more detection apparatus coupled to a processor and a memory, the detection apparatus appropriate to the sensing technology used. The memory may be used to store information such as drop box ID and/or current status. The location of at least a portion of detection apparatus 807 (e.g., the one or more detection apparatus) within drop box 800 may vary from the depiction of FIG. 8, depending upon the type of technology or principle of operation used by detection apparatus 807. Detection apparatus 807 may be communicatively coupled to a wireless transmitter 809, which may communicate the status of drop box 800 via communication link 811 to a monitoring system, e.g., by way of a Wi-Fi link to RF base station 110. Wireless transmitter 809 may be part of drop box 800. Alternatively, a wireless transmitter may be incorporated into patient tags, and the wireless transmitter of a disposable tag that had been deposited into drop box 800 may be used to send the status.

In another embodiment, detection apparatus 807 may include a secondary technology sensor (e.g., an IR monitor or US monitor) that is configured to detect a tag being dropped or otherwise deposited into drop box 800. Detection apparatus 807 also may include a secondary technology emitter matched to the sensor, e.g., an IR emitter that emits signals that can be detected by a paired IR receiver, or a US emitter that emits signals that can be detected by a paired US receiver. A paired emitter and receiver may be physically compatible, e.g., may be incorporated into a single physical housing, such that an emitter portion emits a signal, the signal reflects from or otherwise interacts with an object being detected, and a returned signal is detected by a receiver portion. A paired emitter and receiver also may be functionally compatible, such that the emitted signal is detectable upon return by the paired receiver, e.g., in frequency or wavelength, power level, and timing.

Upon detection by detection apparatus 807 of such a tag, detection apparatus 807 promptly reports via transmitter 809 to a monitoring system that a tag was received. The report may include an identification, e.g., an ID of drop box 800, of the tag, or an ID read from the IR monitor. The monitoring system registers that a tag was dropped into drop box 800. When a count of the number of tags inside drop box 800 reaches a predefined number, a message may be sent in order to request a pickup by a pickup agent. The message may be sent by the monitoring system or by drop box 800 itself.

In some embodiments, detection apparatus 807 may include other types of sensors, such as a sensor to sense an act of opening the closeable opening, or a proximity sensor to sense the patient tag as the patient tag enters the closeable opening, or an indicator that is manually activated by a human user (e.g., a pushbutton switch, touchscreen, etc.).

In some embodiments, the drop box 800 may include an interior space or receptacle 803 for accepting and storing deposited disposable tags. Receptacle 803 is illustrated in phantom in FIG. 8 to indicate that receptacle 803 is inside drop box 800. The interior space of receptacle 803 may be lined with an open mailer 805 that is compatible with a conventional mailing carrier service such as FedEx, UPS, DHL, U.S. Postal Service, etc. The mailer 805 may include a pre-printed destination address, an indication of origin (e.g., a customer, an address, and optionally a secondary locator such as "second floor" or "emergency room"), and either sufficient pre-paid postage or authorization to charge postage to the recipient.

In some embodiments, the drop box 800 may be configured to send an electronic notification via communication link 811 to the mailing carrier service when a mailer 805 is collected for mailing. Such an electronic notification may be useful to inform the carrier and/or recipient that a new mailing is expected. For example, drop box 800 may be stocked with mailers 805 from only one mailing carrier service, and notifications may be pre-programmed to be sent to that mailing carrier service when a mailer 805 has been collected for mailing. In another example, drop box 800 may be stocked with mailers 805 from more than one mailing carrier service. Such mailers 805 may be indicate their respective carriers by use of a machine-readable indicator, e.g., a barcode, an RFID chip, usage of separate receptacles 803 or dispensers of mailers 805 within drop box 800, or the like. Drop box 800 may be configured to read the machine-readable indicator, select the correct destination for the indicated mailing carrier service, and send the notification to the correct mailing carrier service.

In some embodiments, a pickup agent from the correct mailing carrier service may be dispatched to drop box 800 in response to a notification, in order to collect a mailer 805 ready for mailing. In other embodiments, an attendant from the hospital (e.g., a facilities worker, an inventory manager, etc.) may collect a mailer 805 that is ready for mailing, and deposit the mailer 805 at a pickup location for the mailing carrier service.

In some embodiments, a pickup agent, attendant, or the like who collects mailers 805 ready to be mailed, may also bring replacement disposable tags. Such replacement disposable tags may be used to restock a dispenser, or may be transferred to an attendant from the hospital (e.g., an inventory manager, etc.) for further redistribution and usage. Such replacement disposable tags may be temporarily stored in the drop box 800 separately from disposable tags destined for refurbishment.

Embodiments in accordance with the present disclosure may include disposable tags that may be readily marked (e.g., by color coding, inclusion of a "use by" date, etc.) in order to indicate a time limit for usage of the disposable tag before it must be disposed or refurbished. In some embodiments, the disposable tag may be marked with a time period during which it may be recommended for use, e.g., "use during" a specific week of a month, a specific month in a quarter, a specific month in a year, a specific quarter in a year, and so forth. The marking may be by color or pattern, although a profusion of color or pattern choices may be confusing. Instead, the markings may include a textual indicator, such as "use during January 2015", "use during 1Q2015", and so forth. An exemplary marking is illustrated in FIG. 7 as marking 720.

Embodiments in accordance with the present disclosure may include a disposable tag that includes at least a portion of its outer enclosure 406 made from a readily pliable material such as a flexible vinyl. Such a material may offer a desirable combination of strength, resistance to tears or punctures, and patient comfort especially if in contact with skin. The disposable tag with pliable outer enclosure 406 may be sealed with using an RF welding process. RF welding may be known as a process of bonding together materials through the use of electromagnetic energy. Two electrodes create an oscillating electric field that begins to shift and move polar molecules within the materials in order to orient themselves in accordance with the electromagnetic field. The movement of these molecules releases energy in the form of heat. When enough energy is applied, the molecules begin to melt and bond to one another. No external heat is applied. The weld is completed by applying pressure to the bonded area, ensuring a successful seal. Such a disposable tag with pliable shell may further include one or more slits for accepting a wristband, similar to slits 402, 404 illustrated in FIG. 4.

Embodiments in accordance with the present disclosure may include a disposable patient tag having a circuitry layout such that the secondary technology sensor is relatively exposed and able to receive signals with relatively good reception quality when a band is situated on top of the disposable patient tag. FIG. 4, and in particular secondary technology sensor 408, is an example of a disposable patient tag with such a circuitry layout.

The disclosed methods may be readily implemented in software, such as by using object or object-oriented software development environments that provide portable source code that can be used on a variety of computer or workstation platforms. Alternatively, the disclosed system may be implemented partially or fully in hardware, such as by using standard logic circuits or VLSI design. Whether software or hardware may be used to implement the systems in accordance with various embodiments of the present invention may be dependent on various considerations, such as the speed or efficiency requirements of the system, the particular function, and the particular software or hardware systems being utilized.

While the foregoing is directed to embodiments of the present invention, other and further embodiments of the present invention may be devised without departing from the basic scope thereof. It is understood that various embodiments described herein may be utilized in combination with any other embodiment described, without departing from the scope contained herein. Further, the foregoing description is not intended to be exhaustive or to limit the invention to the precise form disclosed. Modifications and variations are possible in light of the above teachings or may be acquired from practice of the invention. Certain exemplary embodiments may be identified by use of an open-ended list that includes wording to indicate that the list items are representative of the embodiments and that the list is not intended to represent a closed list exclusive of further embodiments. Such wording may include "e.g.," "etc.," "such as," "for example," "and so forth," "and the like," etc., and other wording as will be apparent from the surrounding context.

No element, act, or instruction used in the description of the present application should be construed as critical or essential to the invention unless explicitly described as such. Also, as used herein, the article "a" is intended to include one or more items. Where only one item is intended, the term "one" or similar language is used. Further, the terms "any of " followed by a listing of a plurality of items and/or a plurality of categories of items, as used herein, are intended to include "any of," "any combination of," "any multiple of," and/or "any combination of multiples of" the items and/or the categories of items, individually or in conjunction with other items and/or other categories of items.

Moreover, the claims should not be read as limited to the described order or elements unless stated to that effect. In addition, use of the term "means" in any claim is intended to invoke 35 U.S.C. § 112, ¶ 6, and any claim without the word "means" is not so intended.

What is claimed is:

1. A system to collect patient tags for refurbishment, comprising:
   a collection drop box;
   a closeable opening coupled to a wall of the collection drop box, the closeable opening configured to accept patient tags for refurbishment;
   a detection apparatus designed to detect when a patient tag is dropped into the drop box; and
   a communication interface communicatively coupled to the detection apparatus and to a remote monitoring system, the communication interface configured to send a status report to the monitoring system, wherein the communication interface is embedded in the patient tag.

2. The system of claim 1, further comprising a receptacle within the collection drop box, the receptacle configured to store patient tags accepted for refurbishment.

3. The system of claim 1, wherein the detection apparatus comprises a secondary technology emitter.

4. The system of claim 3, wherein the secondary technology emitter is embedded in the drop box.

5. The system of claim 3, wherein the detection apparatus comprises an infrared (IR) emitter.

6. The system of claim 5, wherein a signal from the IR emitter comprises an identification (ID) data, and wherein the status report comprises the ID data.

7. The system of claim 3, wherein the detection apparatus comprises an ultrasound (US) emitter.

8. The system of claim 7, wherein a signal from the US emitter comprises ID data, and wherein the status report comprises the ID data.

9. The system of claim 1, wherein the drop box comprises the communication interface.

10. The system of claim 1, wherein the detection apparatus comprises a detector to sense an act of opening the closeable opening.

11. The system of claim 1, wherein the detection apparatus comprises a proximity sensor to sense the patient tag as the patient tag enters the closeable opening.

12. The system of claim 1, wherein the detection apparatus comprises an indicator that is manually activated by a human user.

13. The system of claim 1, wherein the detection apparatus is configured to determine a status of the collection drop box.

14. The system of claim 13, wherein the communication interface is configured to transmit to a monitoring system a message comprising the status.

15. The system of claim 13, wherein the status of the collection drop box comprises fullness of the receptacle.

16. The system of claim 13, wherein the detection apparatus comprises a counter to count patient tags stored in the receptacle.

17. The system of claim 13, wherein the detection apparatus comprises a scale to weigh patient tags stored in the receptacle, and wherein the communication interface is configured to send a message to the monitoring system if said weight of patient tags reaches a predefined weight.

18. The system of claim 1, wherein the receptacle comprises a pre-printed mailer for a mailing carrier service.

19. The system of claim 1, wherein the communication interface is configured to report the status to a mailing carrier service provider.

20. The system of claim 14, wherein the message comprises an identification of the collection drop box and a request for pickup by the mailing carrier service provider.

21. The system of claim 14, wherein the message comprises a request to deliver refurbished tags to the collection drop box.

22. A system to collect patient tags for refurbishment, comprising:
    a collection drop box;
    a closeable opening coupled to a wall of the collection drop box, the closeable opening configured to accept patient tags for refurbishment; and
    a triggering apparatus within the collection drop box, the triggering apparatus designed to trigger the patient tag to transmit a wireless signal to a remote server, to indicate that the patient tag is in the collection drop box, wherein the patient tag transmits the wireless signal through a communication interface embedded in the patient tag.

23. The system of claim 22, wherein the triggering apparatus comprises a secondary technology transmitter.

24. The system of claim 22, wherein the patient tag comprises a secondary technology receiver.

25. The system of claim 22, further comprising a receptacle within the collection drop box, the receptacle configured to store patient tags accepted for refurbishment.

26. The system of claim 22, wherein the triggering apparatus comprises an infrared (IR) emitter.

27. The system of claim 26, wherein a signal from the IR emitter comprises an identification (ID) data, and wherein the status report comprises the ID data.

28. The system of claim 22, wherein the triggering apparatus comprises an ultrasound (US) emitter.

29. The system of claim 28, wherein a signal from the US emitter comprises ID data, and wherein the status report comprises the ID data.

30. The system of claim 22, wherein the triggering apparatus comprises a detector to sense an act of opening the closeable opening.

31. The system of claim 22, wherein the triggering apparatus comprises a proximity sensor to sense the patient tag as the patient tag enters the closeable opening.

32. The system of claim 22, wherein the triggering apparatus comprises an indicator that is manually activated by a human user.

33. The system of claim 22, wherein the triggering apparatus is configured to determine a status of the collection drop box.

34. The system of claim 33, wherein the status of the collection drop box comprises fullness of the receptacle.

35. The system of claim 22, wherein the triggering apparatus comprises a counter to count patient tags stored in the receptacle.

36. The system of claim 22, wherein the triggering apparatus comprises a scale to weigh patient tags stored in the receptacle.

37. The system of claim 22, wherein the receptacle comprises a pre-printed mailer for a mailing carrier service.

38. The system of claim 22, wherein the patient tag is configured to report the status to a mailing carrier service provider.

39. The system of claim 38, wherein the wireless signal comprises an identification of the collection drop box and a request for pickup by the mailing carrier service provider.

40. The system of claim 38, wherein the wireless signal comprises a request to deliver refurbished tags to the collection drop box.

* * * * *